(12) United States Patent
Kawai et al.

(10) Patent No.: US 7,083,616 B2
(45) Date of Patent: Aug. 1, 2006

(54) MEDICAL MANIPULATOR SYSTEM AND OPERATING METHOD THEREOF

(75) Inventors: Toshikazu Kawai, Kashiwa (JP); Kazutoshi Kan, Chiyoda (JP)

(73) Assignee: Hitachi, Ltd., Tokyo (JP)

( * ) Notice: Subject to any disclaimer, the term of this patent is extended or adjusted under 35 U.S.C. 154(b) by 285 days.

(21) Appl. No.: 10/653,084

(22) Filed: Sep. 3, 2003

(65) Prior Publication Data
US 2004/0059322 A1 Mar. 25, 2004

(30) Foreign Application Priority Data
Sep. 4, 2002 (JP) .............................. 2002-258374

(51) Int. Cl.
*A61B 18/18* (2006.01)
(52) U.S. Cl. .............................. 606/41; 606/46; 606/50
(58) Field of Classification Search .................. 606/41, 606/45–50
See application file for complete search history.

(56) References Cited

U.S. PATENT DOCUMENTS

| | | | | |
|---|---|---|---|---|
| 5,190,541 A | * | 3/1993 | Abele et al. ................... | 606/46 |
| 5,383,917 A | * | 1/1995 | Desai et al. ................... | 607/102 |
| 5,709,679 A | * | 1/1998 | Essig et al. ................... | 606/46 |
| 5,885,277 A | * | 3/1999 | Korth ........................... | 606/35 |
| 5,919,191 A | * | 7/1999 | Lennox et al. ................ | 606/48 |
| 6,059,778 A | * | 5/2000 | Sherman ....................... | 606/34 |
| 6,254,598 B1 | * | 7/2001 | Edwards et al. ............... | 606/41 |
| 6,840,938 B1 | * | 1/2005 | Morley et al. ................. | 606/51 |

FOREIGN PATENT DOCUMENTS

| JP | 08-322787 A | 12/1996 |
|---|---|---|
| JP | 10-094545 A | 4/1998 |
| JP | 2001-029353 A | 2/2001 |

* cited by examiner

*Primary Examiner*—Michael Peffley
(74) *Attorney, Agent, or Firm*—Antonelli, Terry, Stout and Kraus, LLP.

(57) ABSTRACT

For stopping bleeding at an incensed wound, quickly, with using a medical manipulator system, having a plural number of manipulators therein, the medical manipulator system comprises manipulators, each having an operation tool, respectively. Onto the operation tools is applied current, alternately, from a positive electrode of a bipolar electric power source. Onto the other operation tool is applied current from a negative electrode of the bipolar electric power source. Driving the operation tool cauterizes a portion of an affected portion, thereby stopping bleeding in a wide region.

8 Claims, 5 Drawing Sheets

MEDICAL MANIPULATOR SYSTEM AND OPERATING METHOD THEREOF

BACKGROUND OF THE INVENTION

The present invention relates to a manipulator system and an operating method thereof, for medical use, and in particular, it relates to a manipulator system having a plural number of pieces of medical manipulators and the operation method thereof.

An example of the conventional electric operating apparatuses for surgery is described, for example, in Japanese Patent Laying-Open No. Hei 10-94545 (1998)<JP-A 10-94545 (1998)>. In the operating apparatus described in this patent document, a high frequency thermocauterectomy electric power device has a monopolar treatment device or tool and/or a bipolar treatment device or tool, electrodes for use in a patient, and a footswitch. And, a frequency oscillator for treatment generates high frequency output of several hundreds KHz to the electrodes for use in treatment, thereby coagulating and stopping bleeding.

Also, it is described, for example, in Japanese Patent Laying-Open No. 2001-29353 (2001), that stanching or hemostasis must be done, as soon as possible, corresponding to sudden bleeding when conducting an surgery operating with using such the treatment tools. In this patent document, while conducting the treatment of the high frequency thermocauterectomy on a vital tissue being put between the monopolar treatment tools and a P plate, monopolar welding is carried out by means of a monopolar conducting means. And an ultrasonic suction apparatus and the monopolar treatment tool are connected to the high frequency thermocauterectomy electric power device, thereby generating a bipolar output between the ultrasonic suction apparatus and the monopolar treatment tools.

Further in Japanese Patent Laying-Open No. Hei 8-322787 (1996), it is described that a hood is provided covering over portions of an endoscope and treatment devices, in particular, in a medical treatment apparatus.

Thus, in the Patent Document 1 mentioned above, there is described that the thermocauterectomy electric power device comprises the monopolar treatment tool and the bipolar treatment tool, and that hemostasis is conducted on an incised wound with using those tools. However, there is no sufficient description, in particular, about conducting the hemostasis thereon, effectively, depending upon the condition of the incised wound. Namely, in a case where the incised wound lies widely in a region and/or when a resistance value changes between the portions on which the treatment tools pressed, there is a possibility that the hemostasis cannot be done with sufficiency if only applying voltages onto the two (2) pieces of treatment tools, as is described in the Patent Document 2 mentioned above.

In the similar manner, in the Patent Documents 2 and 3, there is described that the hemostasis is conducted via the bipolar electric coagulating, by conducting electricity through a pair of bipolar homeostasis means. However, in those Patent Documents 2 and 3, it is not taken into the consideration, to conduct an effective homeostasis, in particular, when the incised wound lies widely in a region and/or when the resistance value changes between the pair of the bipolar hemostasis means.

BRIEF SUMMARY OF THE INVENTION

According to the present invention, being accomplished by taking the drawbacks of the conventional arts mentioned above into the consideration, an object thereof is to provide a medical manipulator system and an operating method thereof, with using of which homeostasis can be made effectively. Other object according to the present invention is to achieve a medical manipulator system and an operating method thereof, enabling the homeostasis over a wide region thereof.

According to the present invention, for achieving the object mentioned above, there is provided a medical manipulator system, comprising: at least three (3) pieces of manipulators, each can be inserted through with an operation tool at a tip thereof; and a bipolar device having a positive output electrode and a negative output electrode, wherein one (1) of said operation tools, being three (3) or more in number thereof, is electrically connected to either the positive output electrode or the negative output electrode thereof, and at least two (2) of the operation tools remaining are electrically connected to an electrode differing from that, to which said one (1) piece of the operation tool is connected.

And, according to the present invention, in the medical manipulator system as described in the above, it is preferable that said manipulators and the operation tools are electrically insulated therefrom, and preferably, it further comprises dividing means for providing an output of the output electrode, to which said two (2) pieces of the operation tools are connected, to those two (2) pieces of the operation tools, alternately, being provided between said bipolar device and said operation tools. Also, according to the present invention, it is preferable that at least one (1) piece of said plural number of the operation tools has a tip portion, which is driven by a metal wire, and further a driver device is provided for driving said metal wire, wherein said driver device has a pulley, on which an end of the metal wire is fixed and a motor for rotationally driving said pulley, and also, in such the instance, it is preferable that said driver device has an electrode attachment portion to be connected to the bipolar device on a side surface thereof.

Also, according to the present invention, for achieving the other object mentioned above, there is provided a medical manipulator system, comprising: a bipolar device having a positive electrode and a negative electrode; two (2) pieces of operation tools connected to said positive electrode; one (1) piece of operation tool connected to the negative electrode; a dividing means for dividing an output of said bipolar device into two (2) outputs being different from each other in phases thereof; two (2) pieces of output boxes for providing the outputs divided to the two (2) operation tools; and three (3) pieces of manipulators, in which said three (3) pieces of the operation tools are inserted through, respectively, wherein an affected portion is cauterized by conducting electricity between the operation tools connected to said positive electrode and said negative electrode, thereby stopping bleeding.

Further, according to the present invention, for achieving the object(s) mentioned above, there is also provided a medical manipulator system having a plural number of operation tools, comprising: a bipolar device having electrodes, being able to output a positive voltage and a negative voltage thereon; an exchanger means for exchange an output of one electrode of said bipolar device in time sequences; and means for applying current from said bipolar device to said operation tools.

Moreover, according to the present invention, for achieving the object(s) mentioned above, there is further provided an operating method for operating a medical manipulator system for conducting hemostasis on an affected portion with using at least three (3) pieces of manipulators, wherein positive voltage is applied alternately onto operation tools positioning at tips of two (2) of those manipulators while negative voltage is applied onto an operation tool positioning at a tip of remaining one (1), comprising the following steps of: positioning the operation tools, onto which the positive voltage is applied on both sides of a portion where the hemostasis should be conducted, while positioning the operation tool onto which the negative voltage is applied in a middle portion of the portion where the hemostasis should be conducted; bringing those operation tools, thereafter, to be in contact with the affected portion; conducting electricity through the three (3) pieces of the tools; and moving the operation tool, onto which the negative voltage is applied, along the portion where the hemostasis should be conducted, so as to cauterize the affected portion, thereby stopping bleeding.

BRIEF DESCRIPTION OF THE SEVERAL VIEWS OF THE DRAWING

Those and other objects, features and advantages of the present invention will become more readily apparent from the following detailed description when taken in conjunction with the accompanying drawings wherein.

DETAILED DESCRIPTION OF THE INVENTION

Figure 1:
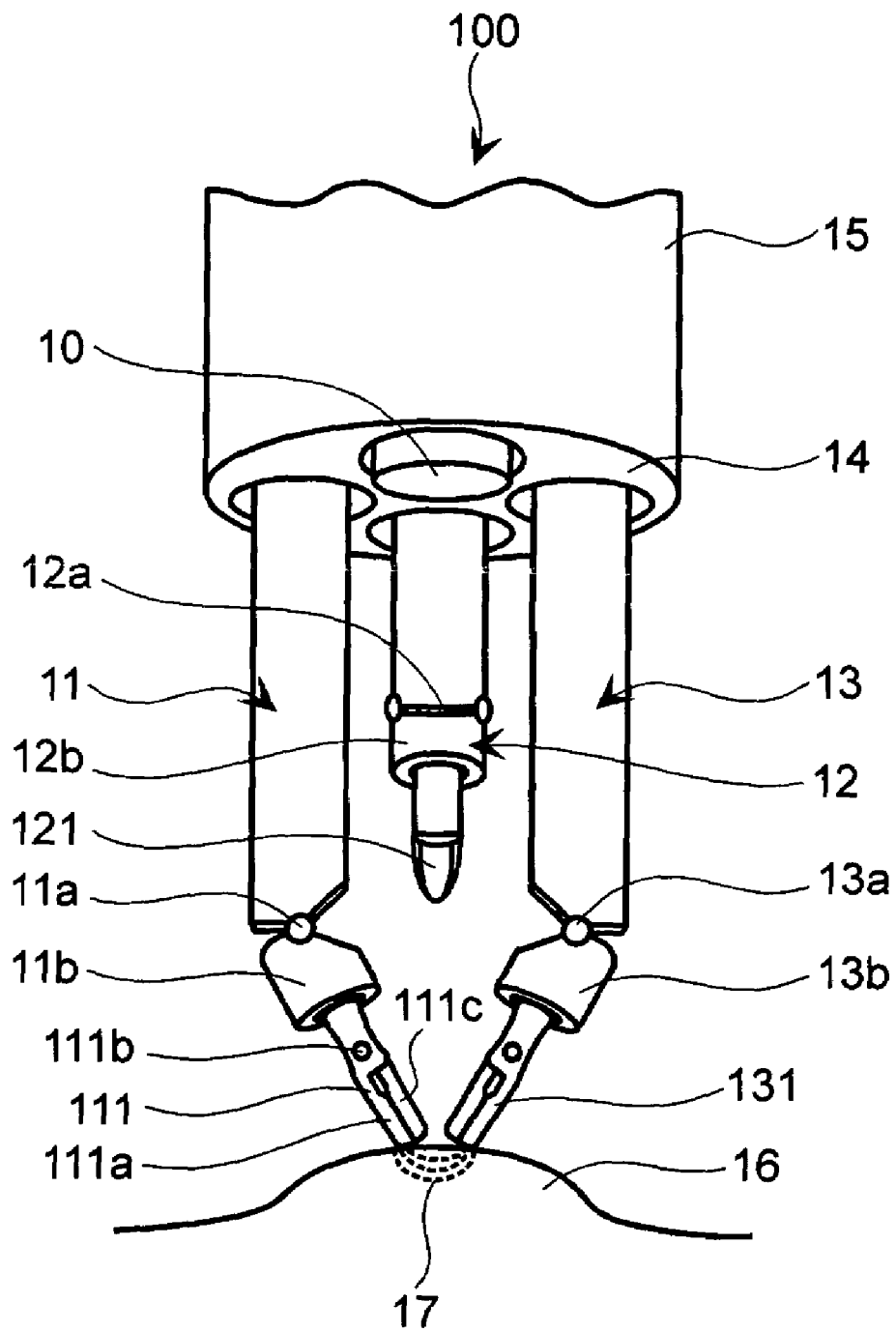
FIG. 1 shows an enlarged perspective view of a principle portion of a medical manipulator system, according to an embodiment of the present invention.

Hereinafter, embodiments according to the present invention will be fully explained by referring to the attached drawings. Herein, FIG. 1 is an enlarged perspective view of a principle portion of a medical manipulator system 100, according to one embodiment of the present invention. The medical manipulator system 100 has an insertion tube or cylinder, in which a plural number of operation tools and/or manipulators can be inserted. The insertion cylinder 15 has a plural number of openings (for example, four (4) positions are formed in FIG. 1). Into one of those openings is inserted an endoscope 10. And into the remaining three (3) openings other than that, into which the endoscope 10 is inserted, manipulators 11 to 13 are inserted, each comprising an operation tool at a tip portion thereof, which will be mentioned later.

Each of the manipulators 11 to 13 has a bending or winding portion 11a to 13a in a middle portion thereof, and each of those bending portion 11a to 13a is located at the position corresponding to a bending portion 212a of the operation tool, which will be mentioned later. Each of portions 11b to 13b, being in a front than those bending portions 11a to 13a, holds one piece of a tip of the operation tool 111, 121 or 131, respectively. The operation tool 111 is a set of forceps, for example, and it comprises a forceps main portion 111a, and a forceps auxiliary or sub-portion 111c, which is attached by a pin supporting portion 111b formed on the forceps main portion 111a, under the condition of being able to open and close between the main portion 111a. Other operation tool 131 is also same to that. The operation tool 121 is a spatula. Those operation tools can be exchanged to scissors and/or a knife depending upon necessity thereof.

Hereinafter, explanation will be given on a principle of hemostasis operation with using the medical manipulator system, being constructed in this manner. An operator not shown in the figure brings the insertion cylinder 15 near to the affected part 16 of a patient. Then, while looking at an image of the endoscope 10, she/he operates the manipulators 11 to 13, thereby treating a microscopic surgery or operation on the affected part 16. Herein, an insulating process is treated on an inner surface of the manipulators 11 to 13, and therefore the operation tools 111, 121 and 131 are insulated from the manipulators 11 to 13, electrically. Accordingly, no electricity flows through the manipulators 11 to 13, even if applying current to the operation tools 111, 121 and 131.

The operation tools 111 and 131 in a pair are connected to a bipolar device (i.e., an electric power source) not shown in the figure, thereby being applicable with a high frequency current thereon. Then, when an incised wound is formed in the affected part 16, tips of the operation tools 111 and 131 are pushed in the vicinity of the incised wound, through which electricity conducts, thereby applying the high frequency current thereto. The portion of the affected part 16, where the high frequency current is applied, is electrically cauterized, thereby forming a hemostatic portion 17. Thereafter, the operation tools 111 and 131 are moved in a direction of the incised wound. With this, the incised wound portion is stanched or stopped from bleeding as a whole thereof. Further, even if the operation tools 111 and 131 are in contact with each other, because of provision of a function of protecting from over-current in the bipolar device, it is possible to prohibit excess current to be applied to the affected part 16. This is the principle of the hemostasis.

Figure 2:
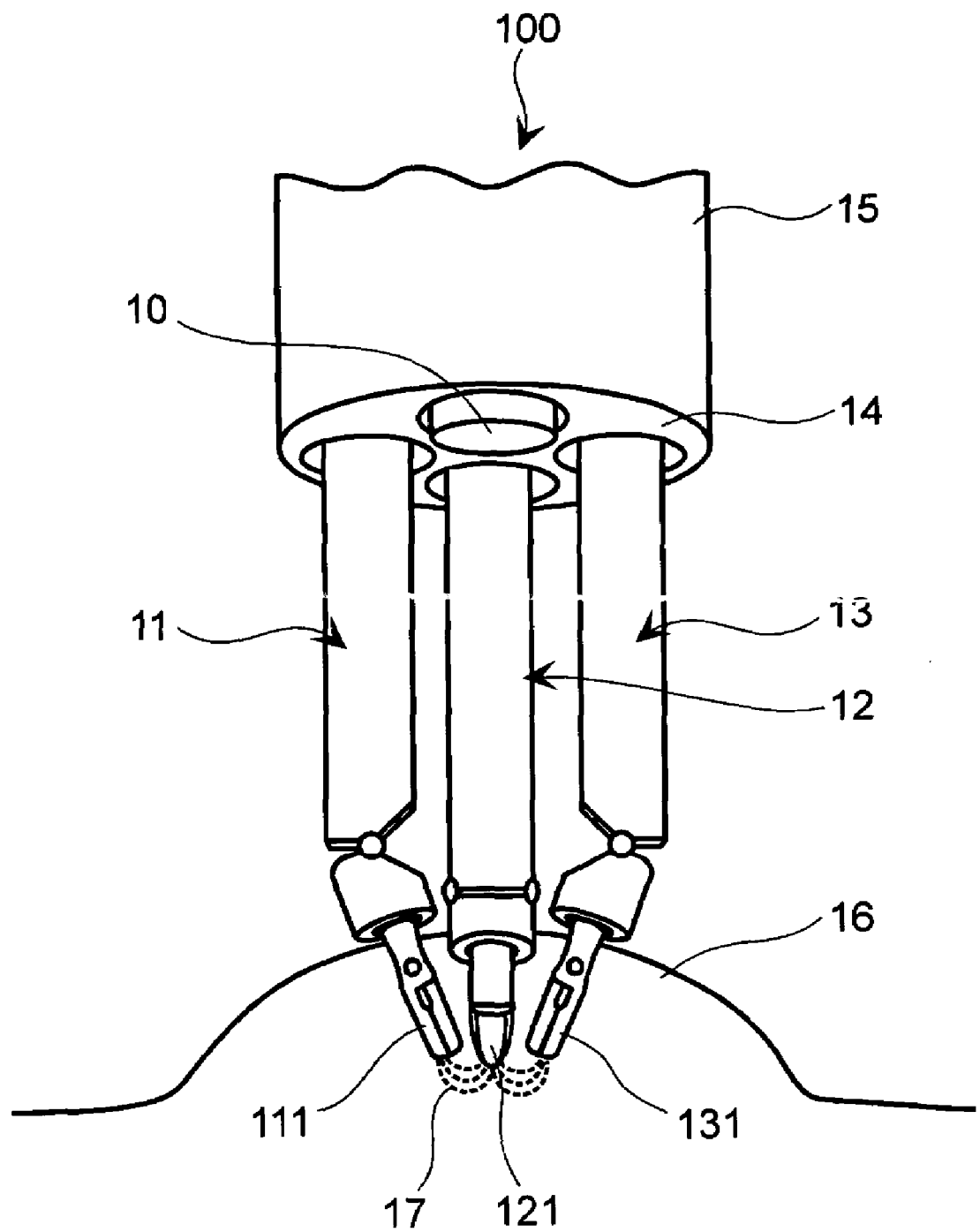
FIG. 2 also shows an enlarged perspective view of the principle portion of the medical manipulator system, according to the embodiment of the present invention.
Figure 3A:
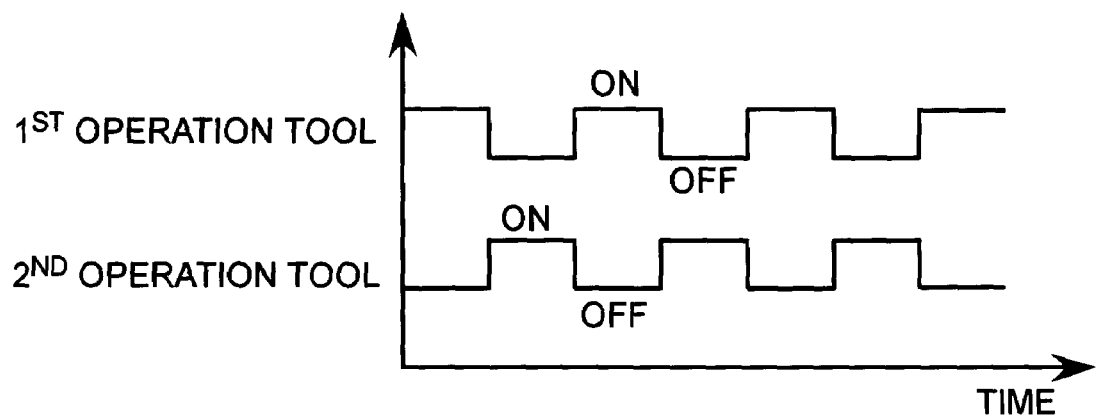
FIGS. 3(a) and (b) show electric circuitry to be used in the medical manipulator system shown in FIG. 2, and operations thereof, for explanation thereof, respectively.
Figure 3B:
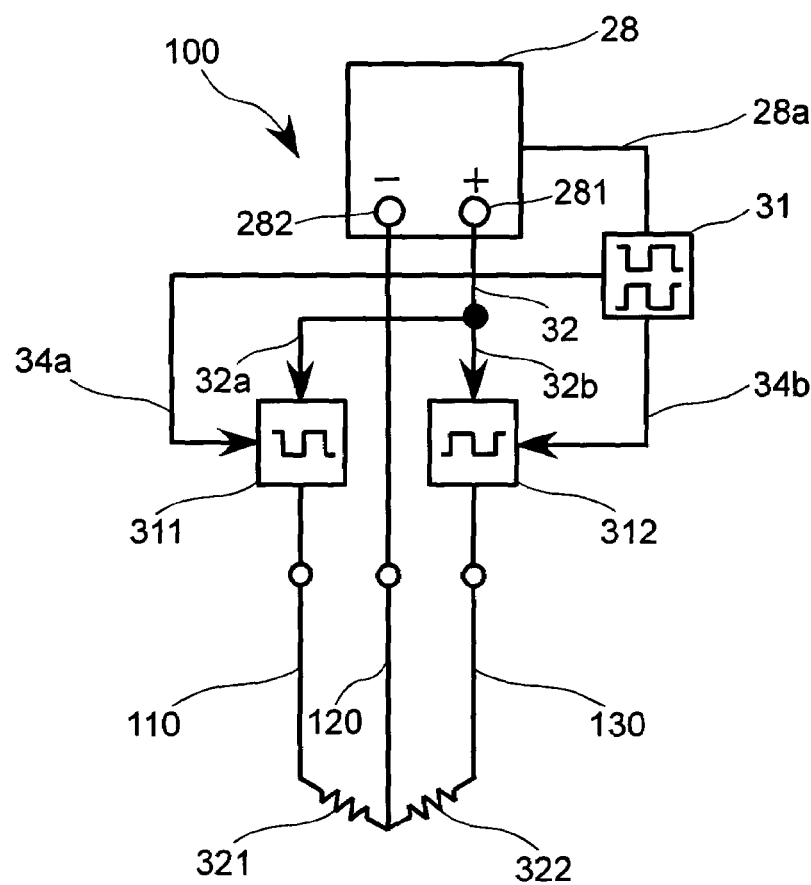
Figure 4A:
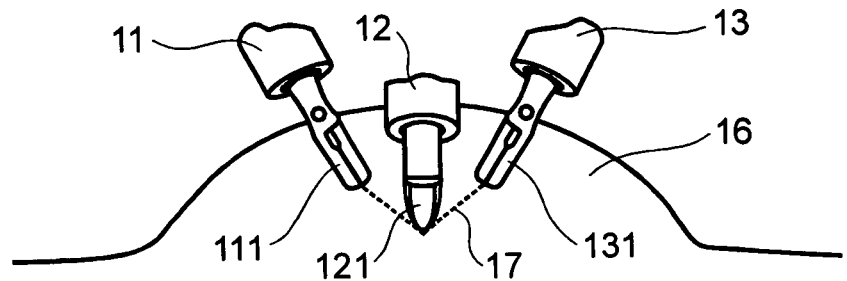
FIGS. 4(a) to 4(c) are explanatory views for showing hemostasis operation with using the medical manipulator system shown in FIG. 2.
Figure 4B:
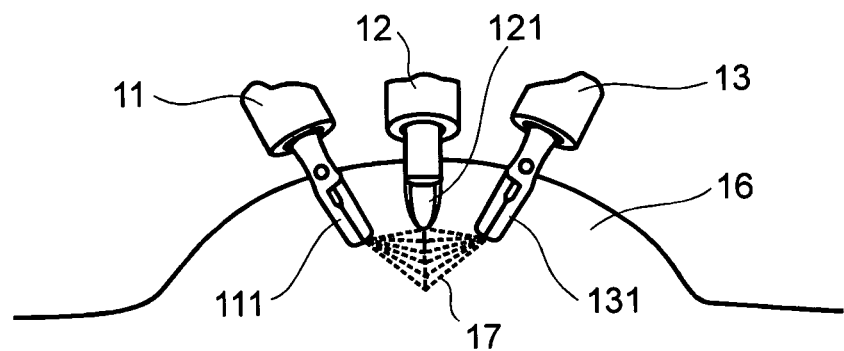
Figure 4C:
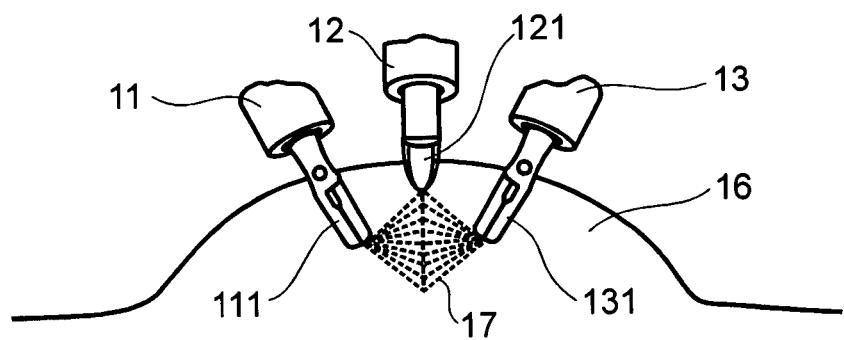
Figure 5A:
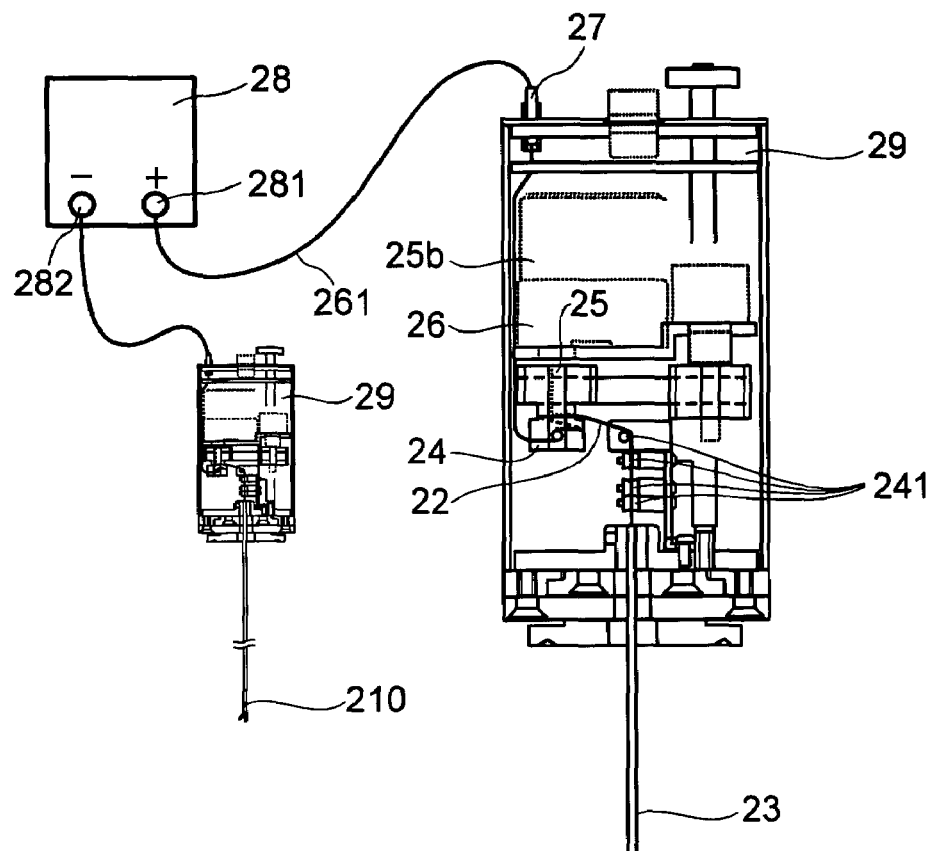
FIGS. 5(a) and 5(b) are a front view for showing the details of the medial manipulator system, and an enlarged view of a portion thereof.

Next, explanation will be given on a hemostasis method over a wide region, with using the medical manipulator system, according to the present invention, by referring to FIG. 2. Herein, FIG. 2 is a perspective view of a principle portion of the medical manipulator system. FIG. 3(b) shows an equivalent electric circuitry of the medical manipulator system, and FIG. 3(a) a time chart thereof. FIGS. 4(a) to 4(c) are views for explaining the hemostasis method with using the manipulator system shown in FIG. 2, and FIG. 5(a) is a front view of the principle portion of the manipulator system according to the present invention.

In FIG. 2, the three (3) pieces of the operation tolls 111, 121 and 131 are connected to the bipolar device, but not shown in the figure, and then current can blow through all of them. Namely, a pair of the forceps 111 and 131 is positioned on both sides of the incised wound on the affected part 16, while the spatula-like tool 121 in the very vicinity of the incised wound portion. After pushing those operation tools 111, 121 and 131 on the affected part 16, current is supplied to all of those operation tools 111, 121 and 131, thereby stopping bleeding or obtaining the hemostasis thereon. The equivalent circuitry of the manipulator system 100 to be used in this hemostasis method and the time chart thereof are shown in FIGS. 3(a) and 3(b).

Each of the manipulators 110 to 130, on which the operation tool is attached, is electrically connected to the bipolar device 28. An output 28a of the bipolar device 28 is guided to a dividing means 31. In this dividing means 31, two (2) signals are produced from the output 28a, which are completely reversed in the phases thereof. And, a signal 34a is supplied to the one output box 311, while a signal 34b being reversed in the phase thereof to the other output box 312. On a while, output current 32 from a positive electrode 281 of the bipolar device 28 is also divided into current 32a and 32b, and they are inputted into the output boxes 311 and 312, respectively.

The output box 311 superimposes the input 34a and the input 32a on each thereof, so as to output the signal superimposed to the manipulator 110. In the similar manner, the output box 312 superimposed the input 34b and the input 32b on each thereof, so as to output the signal superimposed to the manipulator 130. When outputting signals from those output boxes 311 and 312 to the manipulators 110 and 130, while the output is provided to one of the manipulators, no output is provided to the other manipulator. Namely, to the manipulators 110 and 130 is outputted the current, alternatively, in the time sequences thereof. A negative electrode 282 of the bipolar device is connected to the manipulator 120, directly.

When bringing the two (2) pieces of the manipulators 110 and 120, each having the operation tool at the tips portion thereof, to be in contact with the affected portion 16, a resistance 321 can be obtained as an electric resistance of the affected portion 16. In the similar manner, when bringing the two (2) pieces of the manipulators 120 and 130, each having the operation tool at the tips portion thereof, to be contact with the affected portion 16, a resistance 322 can be obtained as an electric resistance of the affected portion 16. When an electric power source of the bipolar device 28 is turned ON under this condition, current is applied to the resistances 321 and 322, alternately, between the positions where the operation tools are in contact with, and therefore the portion having a high resistance value generates heat to cauterize. With this, the hemostasis can be obtained if the cauterized portion is the incised wound.

The resistances 321 and 322 change the resistance values thereof in relation to the positions of the manipulators 110 to 130. In the present embodiment, since currents are produced, being different from each other in the phases thereof, by means of the dividing means 31, thereby changing the conduction conditions to the operation tools attached at the tips of the manipulators 110 and 130, alternately, as shown in FIG. 3(a), therefore the hemostasis operation can be carried out without interruption thereof.

Namely, when electricity conducts through a first operation tool, which is attached on the manipulator 110, the electric conduction to a second operation toll is stopped, which is attached on the manipulator 130. On the contrary, when the electric conduction is stopped through the first operation tool, electricity conducts through the second operation tool. In this time, a third operation tool attached on the manipulator 120 is always at a potential of the negative electrodes 282. Further, the time period during when the dividing means 31 conducts or stops the electricity through the first or the second operation tool is only about several msec. to several sec. in the order thereof.

In the present embodiment, the two (2) manipulators 110 and 130 are made to be the positive pole while the manipulator 120 the negative pole, however it is needless to say that any two of the manipulators can be made to be the positive pole while the other the negative pole. It is also possible to reverse the relationship between the positive pole and the negative pole.

Explanation will be made by referring to FIGS. 4(a) to 4(c), in particular, on the hemostasis method, with using the manipulator apparatus mentioned above, but in more details thereof. In those FIGS. 4(a) to 4(c), there is shown an example, where the hemostasis is conducted over a wide region, such as, 10 to 20 mm in width thereof, for example. At the tip of the manipulator 11 is attached the set of forceps 111, and also at the tip of the manipulator 13 the set of forceps 113. Those sets of forceps 111 and 113 are connected to the positive electrode of the bipolar device 28. The manipulator 12 is attached with the spatula-like tool 121 at the tip thereof, and it is connected to the negative electrode of the bipolar device.

First, as shown in FIG. 4(a), the sets of forceps 111 and 131, which are connected to the positive pole, are brought in contact with the affected portion 16, locating on both sides of the portion of the incised wound formed on the affected portion 16. Then, the spatula-like tool 121, which is connected to the negative pole, is brought in contact with the vicinity of an end portion of the incised wound. Under this condition, the electric power source of the bipolar device 28 is turned ON. Current is applied between the forceps 121 and the operation tool 111 or between the operation tool 121 and the forceps 131, alternately. The portion 17 where the current is applied on the affected portion 16 is cauterized, thereby stopping bleeding or the hemostasis.

Next, as shown in FIG. 4(b), while continuing to apply current thereto, only the manipulator 12 having the operation tool 121 connected to the negative pole is moved into direction of the incised wound. As the operation tool 121 shifts the position thereof, the cauterization is conducted, alternately, i.e., between the operation tool 121 and the forceps 111, or between the operation tool 121 and the forceps 131. With this, the surface-like hemostasis portion 17 is formed on the affected portion 16. When the operation tool 121 reaches up to a position exceeding an end of the incised wound, the hemostasis portion 17 is formed widely in the region, as shown in FIG. 4(c), at the end.

Figure 5B:
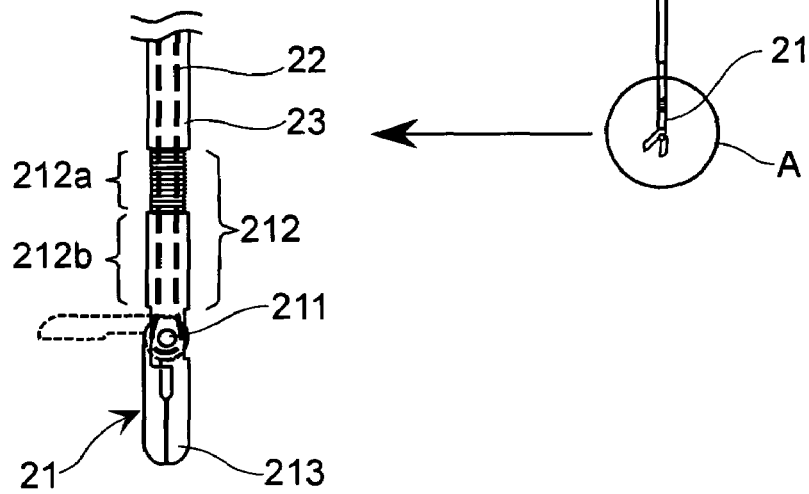

FIGS. 5(a) and 5(b) show the details of one embodiment of the operation tools to be inserted into the manipulator. FIG. 5(a) shows one of the two (2) pieces of the operation tools, being enlarged for showing the details thereof. FIG. 5(b) is the detailed view of a tip portion A thereof. As is shown in this FIG. 5(b), the operation tool 21 is the set of forceps, having a rotating member 211 formed to be rotatable around one end thereof and a member 213 enabling to hold an object between this and the rotating member 211.

Around the rotating member 211 is wound a metal wire 22, while being fixed at one end thereof. When rotating the rotating member 211, the metal wire 22 is pulled up. The member 213 is connected to a forceps base portion 212a, which can be bent, and the set of forceps base portion 212a is connected to a cylinder-like sheath 23. The metal wire 22 for rotating the rotating member 211 is guided to an operation tool driver portion 29 passing through an inside of the sheath 23.

Within an inside of an operation tool driver portion 29, a plural number of pulleys 24 and 241 are attached. On the pulley 24 locating at the forefront of the wire, the metal wire 22 is fixed at the other end thereof and is also wound around it. The pulley 24 is attached on a pulley support shaft 25. The pulley 24 winds up or winds off the metal wire 22 therearound, being driven by a motor 25b attached on the pulley support shaft 25. In this instance, the other plural pulleys 241 achieve a function as a guide for the metal fire 22.

In an inside of the sheath 23 is treated insulating processing. In the similar manner, the insulating processing is treated in an inside of the pulley 24. On one side surface of the operation tool driver portion is attached an electrode attachment portion 27 for inputting current from the positive electrode 28 of the bipolar device 28 through a wire 261. The pulley 24 and an electrode attachment portion 27 are connected with each other through a wire 26. The pulley 241, being positioned within an inside of the operation tool driver potion 29 and on a route being in contact with the wire 22, is made of an insulating material.

Current from the output electrode 281 of the bipolar device 28, which is guided to the pulley 24 through the wire 26, flows through the metal wire 22 to the operation tool 21. The surfaces of the operation tool base portions 212a and 212b are also treated with the insulation processing, therefore no current flows through the manipulators 11 to 13 even if applying current under the condition where the manipulators 11 to 13 are inserted therein.

Other operation tool driver potion 29 is attached at the negative electrode 282 of the bipolar device 28, and current is applied thereto, in the similar manner. If bringing the tip portions of the operation tools 210 and 21 into contact with the affected portion 16 shown in FIG. 1, they functions as the operation tools having the bipolar function, thereby stop bleeding at the incensed wound. However, for obtaining such the hemostasis operation on a wire region, as sown in FIG. 2, it is enough to provide the circuitry shown in FIG. 3(b) in any one of the two (2) output electrodes 281 and 282 of the bipolar device 28 while connecting two (2) or more of the operation tool driver potions to the one of the electrodes thereof.

As was fully explained in the above, according to the present invention, in the manipulator apparatus for use in an operation, since the operation tool locating at the tip portion of the manipulator has the bipolar function; it is possible to conduct the hemostasis operation through such the microscopic operation with ease. Also, by using the operation tools of three (3) pieces or more in the number thereof, the hemostasis operation can be obtained on a wide region.

The present invention may be embodied in other specific forms without departing from the spirit or essential feature or characteristics thereof. The present embodiment(s) is/are therefore to be considered in all respects as illustrative and not restrictive, the scope of the invention being indicated by the appended claims rather than by the forgoing description and range of equivalency of the claims are therefore to be embraces therein.

What is claimed is:

1. A medical manipulator system, comprising:
    an insertion tube having at least a distal end;
    a plurality of openings formed on a surface of said distal end;
    at least three manipulators, each said manipulators being movably mounted within a respective one of said plurality of openings, each said manipulators being independently movable, and each said manipulators including a corresponding operation tool removably mounted at a tip thereof; and
    a bipolar device having a positive output electrode and a negative output electrode for providing a high frequency current therebetween;
    wherein one or more of said at least three manipulators is electrically connected to the positive output electrode, and the remaining manipulators of said at least three manipulators is electrically connected to the negative output electrode.

2. A medical manipulator system, as described in the claim 1, wherein said manipulators are electrically insulated from said operation tools.

3. A medical manipulator system, as described in the claim 1, further comprising dividing means for receiving an output of one of the output electrodes, and producing two output signals reversed in phase from each other.

4. A medical manipulator system, as described in the claim 1, wherein:
    at least one of the operation tools includes a tip portion, and
    wherein said medical manipulator system further comprises a driver device for controlling each tip portion, each said driver device including a metal wire having one end attached to said tip portion, a pulley attached to a second end of said metal wire, and a motor for rotationally driving said pulley.

5. A medical manipulator system, as described in the claim 4, wherein each said driver device further comprises an electrode attachment portion capable of being connected to the bipolar device.

6. A medical manipulator system, comprising:
    a bipolar device having a positive electrode and a negative electrode;
    two operation tools connected to said positive electrode;
    a third operation tool connected to the negative electrode;
    a dividing means for dividing an output of said bipolar device into two outputs having different phases;
    two output boxes for directing the two outputs of said dividing means to said two operation tools; and
    three manipulators for respectively receiving said three operation tools;
    said manipulators being independently movable;
    wherein an affected portion is cauterized by conducting electricity between the operation tools connected to said positive electrode and said negative electrode, thereby stopping bleeding.

7. A medical manipulator system having a plural number of operation tools, comprising:
    a bipolar device having electrodes capable of outputting a positive voltage and a negative voltage;
    an exchanger means for exchanging a phase of an output of one electrode of said bipolar device in time sequences; and
    means for applying current from said bipolar device to said operation tools.

8. An operating method for operating a medical manipulator system to conduct hemostasis on an affected portion, the medical manipulator system including at least three manipulators that are independently movable, wherein positive voltage is applied alternately onto operation tools positioned at tips of two of said at least three manipulators while negative voltage is applied onto an operation tool positioned at a tip of said remaining at least three manipulators, the method comprising the steps of:
    independently positioning two of the operation tools, onto which the positive voltage is applied on two sides of a portion where the hemostasis should be conducted, while independently positioning one operation tool onto which the negative voltage is applied near a center of the portion where the hemostasis should be conducted;
    bringing the operation tools into contact with the affected portion;
    conducting electricity through the operation tools; and
    moving the operation tool, onto which the negative voltage is applied, along the portion where the hemostasis should be conducted, so as to cauterize the affected portion, thereby stopping bleeding.

* * * * *